Figure 1:
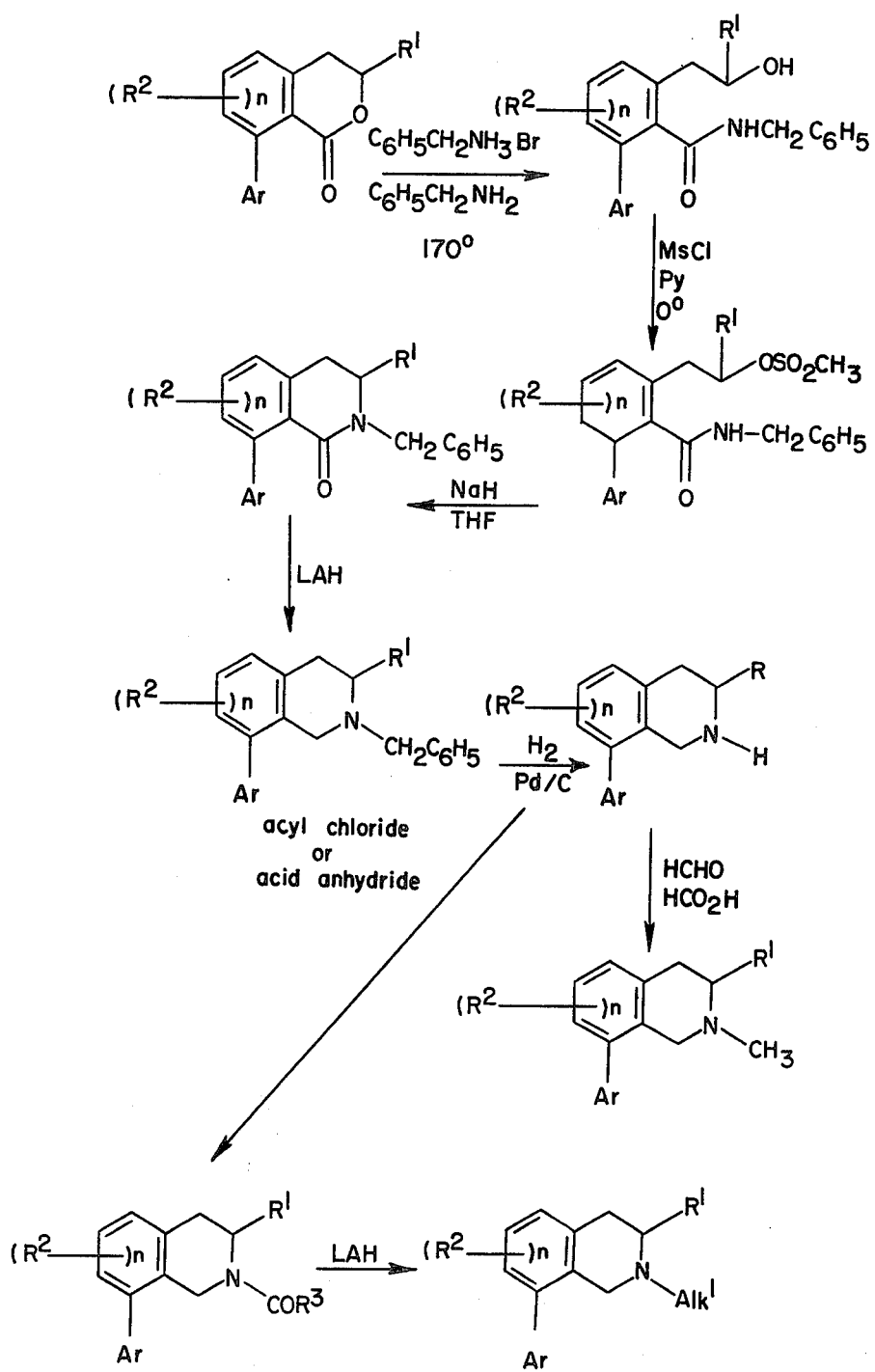

United States Patent [19]

Ellefson et al.

[11] 4,220,778
[45] Sep. 2, 1980

[54] 8-ARYL-1,2,3,4-TETRAHYDROISOQUINO-LINE AND DERIVATIVES THEREOF

[75] Inventors: Charles R. Ellefson, Chicago; Kathleen Prodan, Wheeling, both of Ill.

[73] Assignee: G. D. Searle & Co., Skokie, Ill.

[21] Appl. No.: 956,467

[22] Filed: Oct. 30, 1978

[51] Int. Cl.² .................. C07D 217/04; C07D 217/18
[52] U.S. Cl. .................................... 546/150; 546/139; 546/149; 546/141; 546/146; 260/343.44; 260/559 D; 260/558 S; 260/559 R; 548/237; 548/239; 424/258
[58] Field of Search ............... 546/149, 150, 151, 139

[56] References Cited
PUBLICATIONS

Ahmad et al., "J. Chem. Soc.," 3882–3885, (1961).

*Primary Examiner*—Glennon H. Hollrah
*Attorney, Agent, or Firm*—Dragan Karadzic

[57] ABSTRACT

8-Aryl-1,2,3,4-tetrahydroisoquinoline and derivatives thereof having the formula

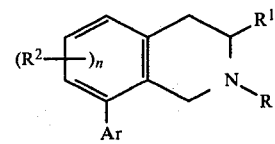

and the non-toxic pharmacologically acceptable acid addition salts thereof; wherein R is hydrogen, benzyl, or an alkyl radical of 1 to 7 carbon atoms; $R^1$ is hydrogen or an alkyl radical of 1 to 7 carbon atoms; $R^2$ in each occurrence is hydrogen, an alkyl radical of 1 to 7 carbon atoms or alkoxy radical of 1 to 7 carbon atoms, alike or different; Ar is phenyl optionally substituted with one or more halogen, an alkyl radical of 1 to 7 carbon atoms, or alkoxy radical of 1 to 7 carbon atoms; and n is positive integer less than 4, are disclosed. These compounds are useful because of their anti-arrhythmic, anti-microbial and central nervous system activity.

18 Claims, 2 Drawing Figures

U.S. Patent Sep. 2, 1980 Sheet 1 of 2 4,220,778

8-ARYL-1,2,3,4-TETRAHYDROISOQUINOLINE AND DERIVATIVES THEREOF

The present invention relates to 8-aryl-1,2,3,4-tetrahydroisoquinoline and derivatives thereof having the following general formula

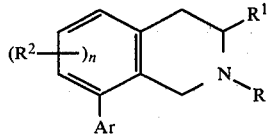

and the non-toxic pharmacologically acceptable acid addition salts thereof; wherein R is hydrogen, benzyl or an alkyl radical of 1 to 7 carbon atoms; $R^1$ is hydrogen or an alkyl radical of 1 to 7 carbon atoms; $R^2$ in each occurrence is hydrogen, an alkyl radical of 1 to 7 carbon atoms or alkoxy radical of 1 to 7 carbon atoms, alike or different; Ar is phenyl optionally substituted with one or more halogen, an alkyl radical of 1 to 7 carbon atoms, or alkoxy radical of 1 to 7 carbon atoms; and n is positive integer less than 4.

The alkyl radicals of 1 to 7 carbon atoms comprehended by R, $R^1$, $R^2$ and as substituents in the phenyl in the foregoing formula are methyl, ethyl, propyl, butyl, pentyl, hexyl, heptyl and the branched-chain isomers thereof.

The alkoxy radicals of 1 to 7 carbon atoms comprehended by $R^2$ and as substituents in the phenyl in the foregoing formula are methoxy, ethoxy, propoxy, butoxy, pentyloxy, hexyloxy, heptyloxy and the branched-chain isomers thereof.

The halogens comprehended as substituents in the foregoing formula are chlorine, bromine, fluorine and iodine.

The number of the optional substituents in the phenyl called for by the foregoing formula as well as the positioning of these substituents relative to the point of attachment of the phenyl or, where more are present, to each other is not critical, but fewer than 4 are preferred.

The number of $R^2$ substituents called for by the foregoing formula and the positionings of these substituents in the aromatic carbocyclic group is not critical.

The compounds of this invention form non-toxic pharmacologically acceptable acid addition salts with a variety of organic and inorganic acids. Such salts are formed with acids such as sulfuric, phosphoric, hydrochloric, hydrobromic, hydroiodic, sulfamic, citric, lactic, maleic, succinic, tartaric, cinnamic, acetic, benzoic, gluconic, ascorbic and related acids.

Embodiments of the present invention of the formula

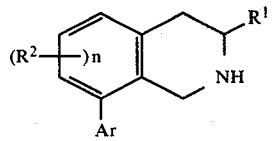

and the non-toxic pharmacologically acceptable acid addition salts thereof; wherein $R^1$ is hydrogen or an alkyl radical of 1 to 7 carbon atoms; $R^2$ in each occurrence is hydrogen, an alkyl radical of 1 to 7 carbon atoms or alkoxy radical of 1 to 7 carbon atoms alike or different; Ar is phenyl optionally substituted with one or more halogen, an alkyl radical of 1 to 7 carbon atoms, or alkoxy radical of 1 to 7 carbon atoms; and n is positive integer less than 4 are preferred.

Further preferred embodiments are compounds of the formula

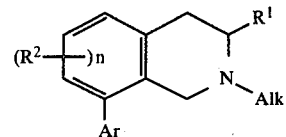

and the non-toxic pharmacologically acceptable acid addition salts thereof; wherein Alk is an alkyl radical of 1 to 7 carbon atoms; $R^1$ is hydrogen or an alkyl radical of 1 to 7 carbon atoms; $R^2$ in each occurrence is hydrogen, an alkyl radical of 1 to 7 carbon atoms or alkoxy radical of 1 to 7 carbon atoms, alike or different; Ar is phenyl optionally substituted with one or more halogen, an alkyl radical of 1 to 7 carbon atoms, or alkloxy radical of 1 to 7 carbon atoms; and n is positive integer less than 4.

Further preferred embodiments are compounds of the formula

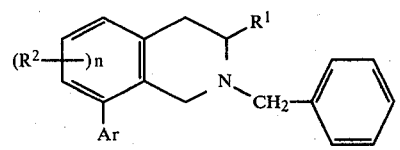

and the non-toxic pharmacologically acceptable acid addition salts thereof; wherein $R^1$ is hydrogen or an alkyl radical of 1 to 7 carbon atoms; $R^2$ in each occurence is hydrogen, an alkyl radical of 1 to 7 carbon atoms or alkoxy radical of 1 to 7 carbon atoms, alike or different; Ar is phenyl optionally substituted with one or more halogen, an alkyl radical of 1 to 7 carbon atoms or alkoxy radical of 1 to 7 carbon atoms, and n is positive integer less than 4.

Further preferred embodiments are compounds of the formula

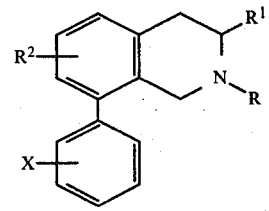

and the non-toxic pharmacologically acceptable acid addition salts thereof; wherein R is hydrogen, benzyl or an alkyl radical of 1 to 7 carbon atoms; $R^1$ is hydrogen or an alkyl radical of 1 7 carbon atoms; and X is hydrogen, halogen, an alkyl radical of 1 to 7 carbon atoms, or alkoxy radical of 1 to 7 carbon atoms; and $R^2$ is hydrogen, an alkyl radical of 1 to 7 carbon atoms or alkoxy radical of 1 to 7 carbon atoms.

Particularly preferred embodiments are compounds of the formula

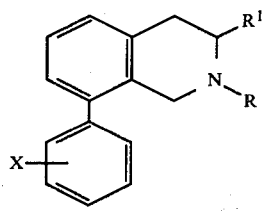

and the non-toxic pharmacologically acceptable acid addition salts thereof; wherein R is hydrogen, benzyl or an alkyl radical of 1 to 7 carbon atoms; $R^1$ is hydrogen or an alkyl radical of 1 to 7 carbon atoms; and X is hydrogen, halogen, an alkyl radical of 1 to 7 carbon atoms or alkoxy radical of 1 to 7 carbon atoms.

The compounds of the present invention are useful because of their pharmacological properties. In particular, they are useful because of their anti-arrhythmic and central nervous system activity. In addition, the compounds of the present invention in which R is benzyl are useful as antimicrobial agents adapted to inhibit or prevent growth of bacteria such as Neisseira gonorrhoeae and protozoa such as Trichomonas vaginalis.

The anti-arrhythmic utility of the present compounds is evident from the results of a standardized test for their capacity to slow the ventricular tachycardia induced by aconitine in the isolated rabbit heart. The procedure is essentially that described by Lucchesi [J. Pharmacol. Exp. Therap., 137, 291 (1962)], modified in certain particulars as follows: Hearts are obtained from adult albino rabbits of either sex and perfused in apparatus modeled after that devised by Anderson and Graves [J. Pharmacol. Exp. Therap., 93, 135 (1968)]. The composition of the perfusion solution is the same as Lucchesi's, but the volume is increased to 200 ml. and the temperature lowered to 28° C. Aconitine (ordinarily as the nitrate) is administered as soon as the heart beat is regular and the EKG pattern normal, the dose being so selected as to at least double the rate. Typically, 0.05 ml. of 0.1% aconitine nitrate in physiological saline is injected. EKG's are recorded at five minute intervals after onset of ventricular tachycardia until two successive readings show stabilization of the rate. Perfusate collected during this time is discarded and replaced with fresh solution q.s. 200 ml. Promptly following stabilization, 2 mgs. of compound dissolved or suspended in 1 ml. of physiological saline is mixed with the perfusion solution. Ten minutes later a like amount is introduced, followed after a further 10 minutes by double the first amount. Final concentration of compound in the perfusion solution is thus 40 mg. per liter. Recording of EKG's is continued at five minute intervals throughout this time and for ten minutes thereafter. A compound is considered anti-arrhythmic if, at any time during the 30 minutes immediately following initial administration in at least half of a minimum of two tests, it reduces by 50% or more the rate recorded ten minutes after onset of tachycardia. Among the compounds of this invention which have been found active in this test are representative compounds 8-phenyl-1,2,3,4-tetrahydroisoquinoline, 2-methyl-8-phenyl-1,2,3,4-tetrahydroisoquinoline, and 2,3-dimethyl-8-phenyl-1,2,3,4-tetrahydroisoquinoline.

The antigonnococcal utility of compounds of this invention can be demonstrated as follows: Sufficient compound is dissolved or suspended in melted chocolate agar to afford, upon serial dilution and mixing with additional melted chocolate agar, concentrations of 100, 10, 1, and 0.1 mcgm/ml. The resultant mixtures are permitted to cool and solidify, then surface-inoculated with a suspension of Neisseria gonorrhoeae ATCC 19424 or ATCC 23050. The inoculated mixtures are incubated at 37° in an atmosphere comprising approximately 10% carbon dioxide for about 48 hours, whereupon they are examined grossly for the presence or absence of test organism growth. Concurrent incubations, identical with the foregoing except that no compound is present, serve as controls. A compound is considered active if, at the maximum concentration tested, no growth of the test organism is visible. Potency is expressed as the minimum concentration at which no growth of the test organism is visible. Potassium penicillin G, inactive in the test as described, was found active against each organism when concentration was increased to 418 mcgm/ml, the procedure being otherwise identical.

The antitrichomonal utility of compounds of this invention can be demonstrated as follows: A modified Diamond medium is prepared by mixing 1200 parts of trypticase (Baltimore Biological Laboratories), 600 parts of yeast extract (Difco), 300 parts of maltose, 60 parts of L-cysteine hydrochloride, 12 parts of L-ascorbic acid, 48 parts of dibasic potassium phosphate, 48 parts of monobasic potassium phosphate, and 54,000 parts of distilled water; adjusting the pH to 6.8 with aqueous 4% sodium hydroxide; incorporating 30 parts of agar (Baltimore Biological Laboratories); boiling for 1 minute to dissolve the agar; and sterilizing, whereupon 80 volumes thereof are diluted with 20 volumes of sterile Dubos medium serum. The resultant medium is inoculated with 1% (by volume) of a 48-hr culture of Trichomonas vaginalis ATCC 30001. Meanwhile, compound is heated in sterile distilled water at a concentration of 1000 mcgm/ml for 20 minutes at 80° C. This compound preparation is serially diluted and mixed with sufficient inoculated medium to afford concentrations of 100, 10, 1, and 0.1 mcgm/ml. The mixtures thus obtained are incubated anaerobically for 48 hr at 37° C. and examined microscopically for the presence of motile trichomonads. Concurrent incubations, identical with the foregoing except that no compound is present, serve as controls. A compound is considered active if, at the maximum concentration tested no motile trichomonads are observed and no aberrancy is apparent in respect of the controls. Metronidazole was found active in this test at 1 mcgm/ml; representative compounds of the present invention 2-benzyl-8-phenyl-1,2,3,4-tetrahydroisoquinoline, 2-benzyl-3-methyl-8-phenyl-1,2,3,4-tetrahydroisoquinoline, 2 -benzyl-8-(m-methoxyphenyl)-1,2,3,4-tetrahydrosoquinoline and 2-benzyl-8-(o-methoxyphenyl)-1,2,3,4-tetrahydroisoquinoline were found active at 100 mcgm/ml in the above tests.

The central nervous activity of the present compounds is evident from their anticonvulsant and antipsychotic activity.

Compounds were evaluated for potential anticonvulsant activity by determining the effect on the hindlimb tonic extensor component of the maximum electroshock seizure pattern in mice according to the method of Swinyard et al. Male Crol: COBS CD-1 (ICR) BR mice weighing 20 to 30 grams were used for this test. Compounds were suspended in saline containing approximately 2% by volume of a 50/50 mixture of propylene glycol and polysorbate-80. A compound or vehicle was administered intraperitoneally to groups of 6 mice.

One-half hour after intraperitoneal treatment, each mouse was challenged with a 50 milliampere electrical current delivered by means of corneal electrodes. This current is sufficient to induce a tonic extensor seizure in 100 percent of control mice. A dose of test compound is rated active if three or more of the treated mice are protected against the hindlimb extensor component of the seizure. Representative compounds of this invention, 2-benzyl-8-(o-methoxyphenyl)-1,2,3,4-tetrahydroisoquinoline, 8-phenyl-1,2,3,4-tetrahydroisoquinoline, 3-methyl-8-phenyl-1,2,3,4-tetrahydroisoquinoline, 8-(o-methoxyphenyl)-1,2,3,4-tetrahydroisoquinoline, 2-methyl-8-phenyl-1,2,3,4-tetrahydroisoquinoline and 2,3dimethyl-8-phenyl-1,2,3,4-tetrahydroisoquinoline are found active in this test at the dose of 64 mg/kg or less.

Antipsychotic activity of the present compounds is evident from the results of the testing of these compounds in tests devised to measure alteration of a conditioned avoidance response in rats, and binding to brain dopamine receptors, using $^3$H-Haloperidol as the ligand.

The training and testing procedures for measuring alteration of a conditioned avoidance response were similar to those described by Potts and East (1971). Eight shuttle cages (Lehigh Valley, Beltsville, Maryland) in sound attenuating cubicles were used to evaluate avoidance behavior. The cages were automatically controlled by a SIGMA 3 computer (Honeywell, Minneapolis, Minn.). Rats were individually placed into the shuttle cage and were allowed to acclimate for approximately one minute. The testing procedure consisted of 100 trials each initiated by a presentation of a conditioned stimulus (CS) consisting of 2800 Hz tone and a light for five seconds. Following this CS, a five second unconditioned stimulus (US) of footshock (approximately 0.2 ma) was delivered to the grid floor of the shuttle cage. Each US was separated from the start of the next trial (CS) by a 15 second intertrial interval (ITI). A shuttle response during this time period resulted in the onset of the CS and US until the rat returned to the other side. Such a response was scored as an intertrial interval response (ITIR). A shuttle response to the opposite side of the cage during the CS terminated the CS and was scored as an avoidance response (AR). A shuttle response during the US terminated the US and was scored as an escape response (ER). Escape latency (EL) was recorded as the period of time between the onset of the US and ER for a rat on a given trial. Failure of a subject to respond within five seconds of the onset of the US was scored as an escape failure (EF). The duration of each 100 trials was approximately 30–35 minutes. Rats were tested on a 100 trial (100 CS presentations) session on alternate days until trained to a criterion of greater than 85% avoidance responses. At least one week after this training, groups of eight rats were given saline containing approximately 2% by volume of a 50/50 mixture of propylene glycol and polysorbate-80 by the intraperitoneal (i.p.) route and 30 minutes later were tested on 100 trials. Two days after this control testing each group was given an i.p. administration of a dose of test drug and 30 minutes later tested on 100 trials. AR, ER, EL, EF and ITIRs were recorded by a SIGMA 3 computer. A compound is considered active if the number of avoidance responses is decreased significantly from control as determined by a Student's test ($P < 0.05$). Representative compounds of this invention 2-benzyl-3-methyl-8-phenyl-1,2,3,4-tetrahydroisoquinoline, 8-phenyl-1,2,3,4-tetrahydroisoquinoline, 8-(o-methoxyphenyl)-1,2,3,4-tetrahydroisoquinoline, 8-(m-methoxyphenyl)-1,2,3,4-tetrahydroisoquinoline, 2-methyl-8-phenyl-1,2,3,4-tetrahydroisoquinoline and 8-(o-methoxyphenyl)-2-methyl-1,2,3,4-tetrahydroisoquinoline are found active in this test at the dose of 40 mg./kg.

$^3$H-haloperidol binding assay procedures described by Burt, et al. Nat. Acad. Sci., 72, 4665 (1975) and Creese, et al. Life Sciences, 17, 993 (1975) were modified as follows. Caudate nuclei were dissected from fresh whole calf brains (Science Associates, Palatine, Ill.) and frozen at $-76°$ C. for up to 6 weeks. Tissue was homogenized in 50 volumes of 0.05 M Tris-HCl buffer, pH 7.7, with a teflon-glass homogenizer. The crude homogenate was centrifuged at $50,000 \times g$ at $4°$ C. for 10 min in a Sorvall RC-2B centrifuge. The tissue pellet was homogenized again in 50 volumes of fresh buffer and recentrifuged at $50,000 \times g$ at $4°$ C. for 10 min. The final pellet was resuspended in 100 volumes of 0.05 M Tris HCl, pH 7.6 containing (in mM): NaCl, 120; KCl, 5; $CaCl_2$, 2; Mg $Cl_2$, 1; paraglyine, 0.01; and 0.1% ascorbate. This final membrane preparation, containing 10 mg original tissue wet weight per ml, was then used to assay for haloperidol receptor binding activity. Specific binding of $^3$H-haloperidol (15.87 Ci/mmole, New England Nuclear Corp., Boston, Mass.) was determined by measuring binding in the absence and presence of $10^{-4}$M unlabelled dopamine.

Samples of the homogenate were preincubated for 5 min. at $37°$ C. After cooling on ice, varying concentrations of standards and test compounds ($10^{-9}$M to $10^{-5}$M) were added to triplicate sample tubes. The reaction was initiated by adding $^3$H-haloperidol (final concentration 1.6 nM) and incubating at $37°$ C. for 10 minutes in a reciprocating water bath. The reaction was terminated by immediately filtering the samples and recovering protein membranes on Whatman GF-B filters under reduced pressure. Trapped membranes were washed twice with 5 ml. of ice-cold Tris-HCl buffer, pH 7.7., then solubilized off the filters using 1 ml NCS tissue solubilizer (Amersham/Searle) at $50°$ C. for 1 hour. Then, pH was adjusted by adding 0.1 ml glacial acetic acid, 10 ml PCS (Amersham/Searle) added and the samples analyzed for membrane-bound radioactivity using a Mark II liquid scintillation counter (Searle Analytic, Inc.). The molar concentration that prevents binding of $^3$H-haloperidol to the brain dopamine receptor by 50% (I.C. 50) of the representative compounds of the present invention and the known standards, chlorpromazine, halperidol and clozapine are given in Table 1.

Table 1

| Compound | I.C. 50 |
| --- | --- |
| 2-benzyl-3-methyl-8-phenyl-tetrahydroisoquinoline | $2.7 \times 10^{-7}$ |
| 8-phenyl-1,2,3,4-tetrahydro-isoquinoline | $1.5 \times 10^{-6}$ |
| 8-(o-methoxyphenyl)-1,2,3,4-tetrahydroisoquinoline | $1.3 \times 10^{-5}$ |
| 8-(m-methoxyphenyl)-1,2,3,4-tetrahydroisoquinoline | $6.5 \times 10^{-7}$ |
| 2-methyl-8-phenyl-1,2,3,4-tetrahydroisoquinoline | $2.7 \times 10^{-8}$ |
| 8-(o-methoxyphenyl)-2-methyl-1,2,3,4-tetrahydroisoquinoline | $6.6 \times 10^{-7}$ |
| chlorpromazine | $3.4 \times 10^{-8}$ |
| haloperidol | $1.8 \times 10^{-9}$ |

Table 1-continued

| Compound | I.C. 50 |
| --- | --- |
| clozapine | 1.8 × 10⁻⁷ |

Results of the standardized biological testing of selected compounds of this invention set forth above are provided solely for purposes of illustration, and accordingly should not be considered as either delimiting or exclusionary.

Compounds of the present invention are prepared by methods set out in FIG. 1, wherein $R^1$, $R^2$, Ar and n are as previously defined $R^3$ is alkyl radical of 1 to 6 carbon atoms, and $Alk^1$ is an alkyl radical of 2 to 7 carbon atoms.

Figure 2:
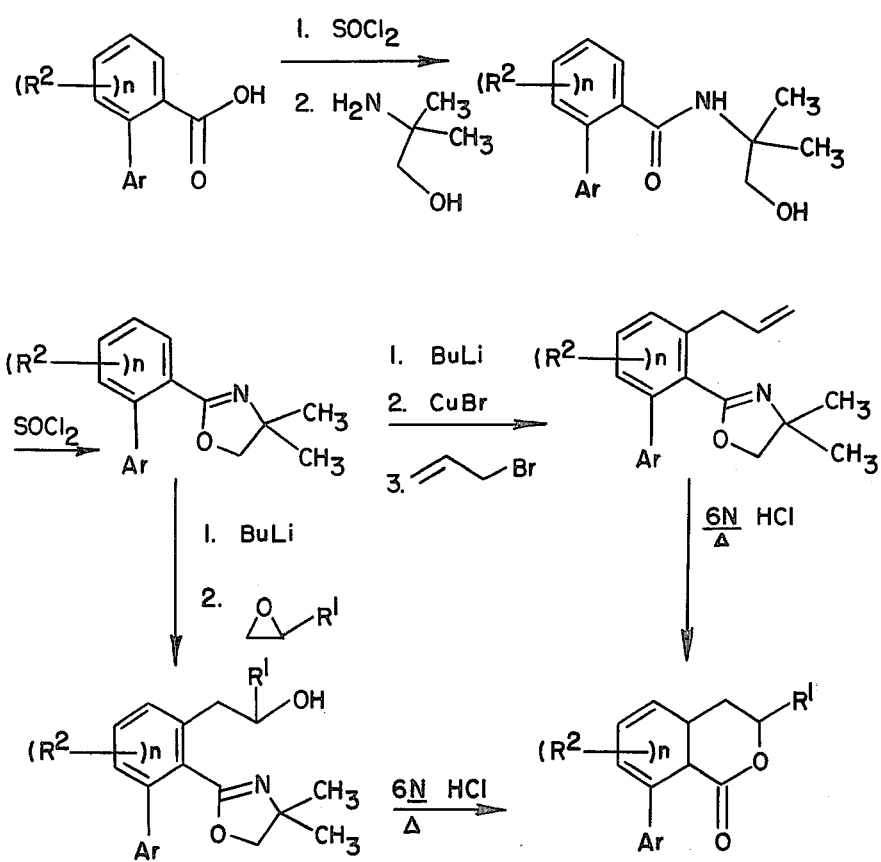

The 8-arylisocoumarin starting materials are prepared using techniques developed by Meyers et al., J. Org. Chem, 40, 3158 (1975) and Gschweld et al., J. Org. Chem., 40, 2008 (1975) as set out in FIG. 2, wherein $R^1$, $R^2$, Ar and n are as previously defined.

Typically, biphenyl-2-carboxylic acid is converted to the acid chloride and reacted with 2-amino-2-methyl propanol to give the corresponding hydroxyamide, which on treatment with thionyl chloride cyclizes to 2-(2-biphenyl)-4,4-dimethyl-2-oxazoline. 2-(2-biphenyl)-4,4-dimethyl-2-oxazoline is metallated with n-butyllithium, converted to the organo-copper reagent with cuprous bromide and alkylated with allyl bromide to give 2-(3-allyl-2-biphenyl)-4,4-dimethyl-2-oxazoline which is then hydrolyzed in refluxing 6 N hydrochloric acid to give 3-methyl-8-phenylisocoumarin. Alternately, 2-(3-allyl-2-biphenyl)-4,4-dimethyl-2-oxazoline is reacted with n-butyllithium and then alkylated with propylene oxide to give 2-[3-(2-hydroxypropyl)-2-biphenyl]-4,4-1 dimethyl-2-oxazoline which is hydrolyzed in refluxing 6 N hydrochloric acid to give 3,4,-dihydro-3-methyl-8-phenylisocoumarin.

Heating 3,4-dihydro-3-methyl-8-phenylisocoumarin and benzylamine hydrobromide in benzylamine at 160° C. gives N-benzyl-6-(2-hydroxy-2-methylethyl)2-biphenylcarboxamide which is converted to the corresponding mesylate and then cyclized to 2-benzyl-3,4-dihydro-3-methyl-8-phenyl-1(2H)-isoquinolone with sodium hydride. This compound is then reduced with lithium aluminum hydride to give 2-benzyl-3-methyl-8-phenyl-1,2,3,4-tetrahydroisoquinoline. Hydrogenation of this product using 5% palladium-on-carbon on the catalyst affords 3-methyl-8-phenyl-1,2,3,4-tetrahydroisoquinoline. Reacting 3-methyl-8-1,2,3,4-tetrahydroisoquinoline with formaldehyde and formic acid affords 2,3-dimethyl-8-phenyl-1,2,3,4-tetrahydroisoquinoline.

The invention will appear more fully from the examples which follow. The examples are not to be construed as limiting the invention either in spirit or in scope as variations both in materials and in methods will be apparent to those skilled in the art. Throughout the examples hereinafter set forth, temperatures are given in degrees Centigrade (°C.) and quantity of materials in parts by weight unless parts by volume is specified.

EXAMPLE 1

6 Parts of biphenyl-2-carboxylic acid is added to 15 parts by volume of thionyl chloride and the mixture is stirred at ambient temperature for about 22 hours. The thionyl chloride is distilled off under reduced pressure, then benzene is added and distilled off under reduced pressure leaving an oil. The oil is dissolved in 15 parts by volume of methylene chloride and added dropwise with stirring to a solution of 5.5 parts of 2-amino-2-methylpropanol in 15 parts by volume of methylene chloride at 0° C. The resultant mixture is stirred at ambient temperature overnight, filtered and the filtrate washed with water, twice with 25 parts by volume of 5% hydrochloric acid, twice with 25 parts by volume of 5% sodium hydroxide, and water. The filtrate is then dried over anhydrous magnesium sulfate and the solvent removed under reduced pressure to give N-(2-hydroxy-1,1-dimethylethyl)-2-biphenylcarboxamide, as white crystals, melting at about 72.5°-74° C. after recrystallization from ether.

10 Parts by volume of thionyl chloride is added in portions with stirring to 11.8 parts of the above compound. After all of the solid has dissolved the solution is stirred for about 20 minutes and poured into 125 parts by volume of anhydrous ether. The solid is washed with ether and dried to give white powder. The white powder is dissolved in water and the resultant solution treated with 50% sodium hydroxide extracted with ether and the extract washed with water and dried over anhydrous magnesium sulfate. The ether is distilled to give a clear colorless oil which is crystallized from a small amount of petroleum ether to give 2-(2-biphenyl)4,4-dimethyl-2-oxazoline, as colorless crystals, melting at about 38.5°-40.5° C. This compound is represented by the following structural formula

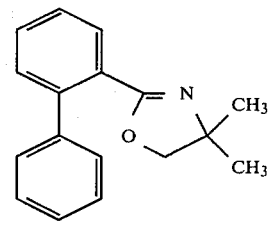

Substitution of an equivalent quantity of the appropriately substituted biphenyl-2-carboxylic acid in the foregoing procedure affords the following compounds:
  2-(2'-methoxy-2-biphenyl)-4,4-dimethyl-2-oxazoline;
  2-(3'-methoxy-2-biphenyl)-4,4-dimethyl-2-oxazoline;
  2-(4'-chloro-2-biphenyl)-4,4-dimethyl-2-oxazoline;
  2-(2'-methyl-2-biphenyl)-4,4-dimethyl-2-oxazoline;
  2-(3'-bromo-2-biphenyl)-4,4-dimethyl-2-oxazoline;
  2-(5-methyl-2-biphenyl)-4,4-dimethyl-2-oxazoline;
  2-(6-methoxy-2-biphenyl)-4,4-dimethyl-2-oxazoline;
  2-(5,6-dimethyl-2-biphenyl)-4,4-dimethyl-2-oxazoline;
  2-(2',5-dimethoxy-2-biphenyl)-4,4-dimethyl-2-oxozoline;

EXAMPLE 2

43 Parts by volume of 2.4 M n-butyllithium in hexane is added dropwise with stirring to a solution of 17.7 parts of 2-(2-biphenyl)-4,4-dimethyl-2-oxazoline in 300 parts by volume of dry tetrahydrofuran at 0° C. and stirring is continued for about 3.5 hours. The resulting deep red solution is added dropwise to a stirred suspension of 14.3 parts of cuprous bromide in 300 parts by volume of dry tetrahydrofuran at 0° C. The deep green mixture is stirred at 0°0 C. for about 1 hour, then 12.1 parts of allyl bromide is added dropwise and stirring is continued for about 1 hour. 50 Parts of water is then added dropwise followed by 100 parts by volume of concentrated ammonium hydroxide. The layers are separated and the aqueous layer washed with ether. The combined organic solutions are washed with saturated aqueous sodium chloride, dried over anhydrous magnesium sulfate and the solvent removed by distillation to give an amber oil. This oil is purified by low pressure chromatography on silica gel using 5% ethyl acetate in benzene as the eluant to yield 2-(3-allyl-2-biphenyl)-4,4-dimethyl-2-oxazoline, as clear oil characterized by infrared absorption maximum in chloroform at 1666cm$^{-1}$. This compound is represented by the following structural formula

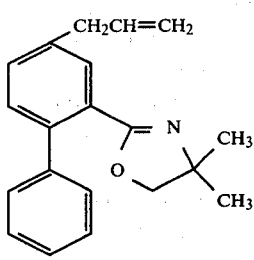

EXAMPLE 3

25 Parts by volume of 2.4 M n-butyllithium in hexane is added dropwise with stirring to a solution of 10 parts of 2-(2-biphenyl)-4,4-dimethyl-2-oxazoline in 200 parts by volume of dry tetrahydrofuran at about −5° C. The resultant deep red solution is stirred at about −5° C. for about 3 hours and, then, a solution of 15 parts by volume of ethylene oxide in 50 parts by volume of dry tetrahydrofuran is added dropwise. The mixture is allowed to warm to ambient temperature, stirred overnight, 50 parts by volume of water added and the layers separated. The organic portion is concentrated under reduced pressure, the residual oil taken up in ether, washed with water and dried over anhydrous magnesium sulfate. The solvent is removed under reduced pressure and the resulting clear amber oil purified by low pressure liquid chromatography to yield oil that solidifies on standing. The solid is recrystallized from the mixture of ethyl acetate and hexane to give 2-[3-(2-hydroxyethyl)-2-biphenyl]-4,4-dimethyl-2-oxazoline, as white crystals melting at about 86.5°-87° C. This compound is represented by the following formula

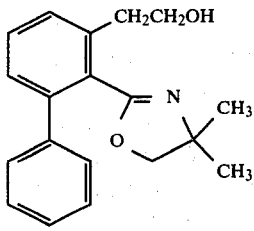

A mixture of 10.2 parts of 2-[3-(2-hydroxyethyl)-2-biphenyl]-4,4-dimethyl-2-oxazoline and 1000 parts by volume of 6N hydrochloric acid is stirred at reflux temperature for about 7 hours and then cooled to ambient temperature. The semi-solid that separates is washed with several portions of water and air dried, to yield tan solid. This solid is recrystallized from the mixture of ethyl acetate and hexane to give 3,4-dihydro-8-phenylisocoumarin, as beige crystals melting at about 105°-106° C. This compound has the following formula

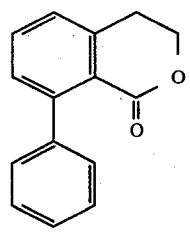

Substituting equivalent quantities of the appropriate 2-oxazoline and the appropriate alkylene oxide for 2-(2-biphenyl)-4,4-dimethyl-2-oxazoline and ethylene oxide called for respectively in the procedure of paragraph 1 and substantially repeating the procedures of the preceding two paragraphs the following compounds are obtained:

3,4-dihydro-3-methyl-8-phenylisocoumarin;
3,4-dihydro-8-(o-methoxyphenyl)isocoumarin;
3,4-dihydro-8-(m-methoxyphenyl)isocoumarin;
8-(p-chlorophenyl)-3,4-dihydroisocoumarin;
3,4-dihydro-8-(o-methylphenyl)isocoumarin;
3,4-dihydro-3-ethyl-8-phenylisocoumarin;
8-(m-bromophenyl)-3,4-dihydroisocoumarin;
3,6-dimethyl-3,4-dihydro-8-phenylisocoumarin;
3,4-dihydro-7-methoxy-8-phenylisocoumarin;
3,4-dihydro-6,7-dimethyl-8-phenylisocoumarin;
3,4-dihydro-7-methoxy-8-(o-methoxyphenyl)isocoumarin;
3,4-dihydro-3-propyl-8-phenylisocoumarin.

EXAMPLE 4

A mixture of 8.06 parts of 2-(3-allyl-2-biphenyl)-4,4-dimethyl-2-oxazoline and 600 parts by volume of 6N hydrochloric acid are stirred at reflux temperature overnight. The solid which separates on cooling is taken up into ether, the ether solution washed with water, dried over anhydrous magnesium sulfate and the solvent removed by distillation to give, as a solid, 3,4-dihydro-3-methyl-8-phenylisocoumarin, melting at about 140°-141.5° C. after recrystallization from ethanol. This compound has the following formula

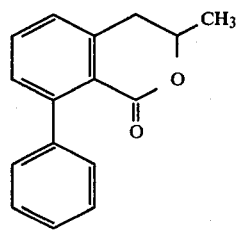

EXAMPLE 5

A mixture of 7.84 parts of 3,4-dihydro-8-phenylisocoumarin and 8 parts of benzylamine hydrobromide in 40 parts by volume of benzylamine is stirred at about 160° C. for about 4 hours. The reaction solution is then cooled and poured into 500 parts by volume of 5% hydrochloric acid. The oil which separates is extracted into methylene chloride and the extracts are washed with several portions of 5% hydrochloric acid, water, dried over anhydrous magnesium sulfate and the solvent removed to give, as a solid, N-benzyl-3-(2-hydroxyethyl)-2-biphenylcarboxamide. The solid is recrystallized from a mixture of chloroform and hexane to give white flocculant crystals melting at about 129°–130° C. This compound has the following formula

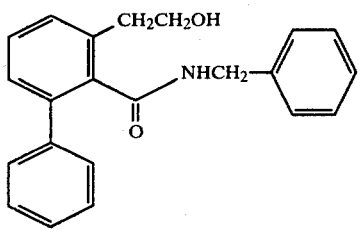

Substitution of an equivalent quantity of the appropriate 3,4-dihydro-8-arylisocoumarin in the above detailed procedure and substantial repetition of that procedure affords the following compounds:
  N-benzyl-3-(2-hydroxypropyl)-2-biphenylcarboxamide, melting at about 94.5°–96° C. after recrystallization from a mixture of ethyl acetate and hexane;
  N-benzyl-2-(2-hydroxyethyl)-2'-methoxy-2-biphenylcarboxamide, melting at about 94°–95° C.;
  N-benzyl-3-(2-hydroxyethyl)-3'-methoxy-2-biphenylcarboxamide, melting at about 106.5°–112° C.;
  N-benzyl-4'-chloro-3-(2-hydroxyethyl)-2-biphenylcarboxamide;
  N-benzyl-3-(2-hydroxyethyl)-2'-methyl-2-biphenylcarboxamide;
  N-benzyl-3-(2-hydroxybutyl)-2-biphenylcarboxamide;
  N-benzyl-3'-bromo-3-(2-hydroxyethyl)-2-biphenylcarboxamide;
  N-benzyl-3-(2-hydroxypropyl)-5-methyl-2-biphenylcarboxamide;
  N-benzyl-3-(2-hydroxyethyl)-6-methoxy-2-biphenylcarboxamide;
  N-benzyl-3-(2-hydroxyethyl)-5,6-dimethyl-2-biphenylcarboxamide;
  N-benzyl-3-(2-hydroxyethyl)-2',6-dimethoxy-2-biphenylcarboxamide; and
  N-benzyl-3-(2-hydroxypentyl)-2-biphenylcarboxamide.

EXAMPLE 6

A solution of 15 parts of N-benzyl-3-(2-hydroxyethyl)-2-biphenylcarboxamide in 150 parts by volume of pyridine is cooled in an ice bath and 10.5 parts of mesyl chloride is added and the resultant mixture is left in the refrigerator overnight. Then, the mixture is diluted to 500 parts by volume with ice water. On stirring an oil separates and solidifies. The solid is washed with several portions of water and air dried to give N-benzyl-3-(2-methylsulfonyloxyethyl)-2-biphenylcarboxmide, as light tan powder, melting at about 108°–110° C. This compound has the following formula

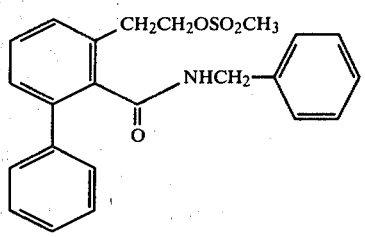

Substitution of an equivalent quantity of the appropriate 2-biphenylcarboxamide in the above detailed procedure and substantial repetition of that procedure affords the following compounds:
  N-benzyl-3-(2-methylsulfonyloxypropyl)-2-biphenylcarboxamide, as white powder melting at about 107°–109.5° C.;
  N-benzyl-2'-methoxy-3-(2-methylsulfonyloxyethyl)-2-biphenylcarboxamide;
  N-benzyl-3'-methoxy-3-(2-methylsulfonyloxyethyl)-2-biphenylcarboxamide;
  N-benzyl-4'-chloro-3-(2-methylsulfonyloxyethyl)-2-biphenylcarboxamide;
  N-benzyl-3-(2-methylsulfonyloxyethyl)-2'-methyl-2-biphenylcarboxmide;
  N-benzyl-3-(2-methylsulfonyloxyfutyl)-2-biphenylcarboxamide;
  N-benzyl-3'-bromo-3-(2methylsulfonyloxyethyl)-2-biphenylcarboxamide;
  N-benzyl-3-(2-methylsulfonyloxypropyl)-5-methyl-2-biphenylcarboxamide;
  N-benzyl-6-methoxy-3-(2-methyldulfonyloxyethyl)-2-biphenyl-carboxamide;
  N-benzyl-5,6-dimethyl-3-(2-methylsulfonyloxyethyl)-2-biphenyl carboxamide;
  N-benzyl-2',6-dimethoxy-3-(2-methylsulfonyloxyethyl)-2-biphenylcarboxamide; and
  N-benzyl-3-(2-methylsulfonyloxypentyl)-2-biphenylcarboxamide.

EXAMPLE 7

A mixture of 17.5 parts of N-benzyl-3-(2-methylsulfonyloxyethyl)-2-biphenylcarboxamide and 5 parts of 50% sodium hydride dispersion in oil in 200 parts by volume of dry tetrahydrofuran is stirred at reflux temperature overnight. Then, the reaction mixture is cooled and water added dropwise to decompose the excess hydride. The solvent is removed under reduced pressure, the residue taken up in methylene chloride, washed with water and dried over anhydrous magnesium sulfate. Methylene chloride is removed under reduced pressure to yield 2-benzyl-3,4-dihydro-8-phenyl-1(2H)-isoquinoline, melting at about 137.5°–138.5° C. after recrystallization from a mixture of ethyl acetate and hexane. This compound has the following formula

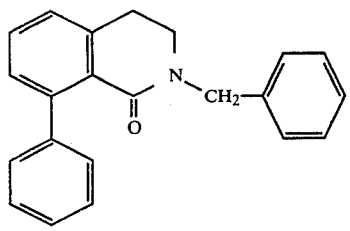

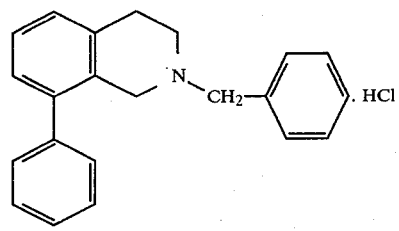

Substitution of an equivalent quantity of the appropriate N-benzyl-3-(2-methylsulfonyloxyalkyl)-2-biphenylcarboxamide in the above detailed procedure and substantial repetition of that procedure affords the following compounds:

2-benzyl-3,4-dihydro-3-methyl-8-phenyl-1(2H)-isoquinoline, melting at about 112°-113° C. after recrystallization from cyclohexane;

2-benzyl-3,4-dihydro-8-(o-methoxyphenyl)-1(2H)-isoquinoline;

2-benzyl-3,4-dihydro-8-(m-methoxyphenyl)-1(2H)-isoquinoline;

2-benzyl-8-(p-chlorophenyl)-3,4-dihydro-1(2H)-isoquinoline;

2-benzyl-3,4-dihydro-8-(m-methylphenyl)-1(2H)-isoquinolone;

2-benzyl-3-ethyl-3,4-dihydro-8-phenyl-1(2H)-isoquinolone;

2-benzyl-8-(m-bromophenyl)-3,4-dihydro-1(2H)-isoquinolone;

2-benzyl-3,4-dihydro-3,6-dimethyl-8-phenyl-1(2H)-isoquinolone;

2-benzyl-3,4-dihydro-7-methoxy-8-phenyl-1(2H)-isoquinolone;

2-benzyl-3,4-dihydro-6,7-dimethyl-8-phenyl-1(2H)-isoquinolone;

2-benzyl-3,4-dihydro-7-methoxy-8-(o-methoxyphenyl)-1(2H)-isoquinolone; and 2-benzyl-3,4-dihydro-8-phenyl-3-propyl-1(2H)-isoquinolone.

EXAMPLE 8

3.6 Parts of lithium aluminum hydride is added to a solution of 10 parts of 2-benzyl-3,4-dihydro-8-phenyl-1(2H)-isoquinolone in 225 parts by volume dry tetrahydrofuran and the resulting mixture is stirred at reflux temperature for about 5 hours. Then the mixture is cooled in an ice bath and treated successively with 7.5 parts by volume of water in 15 parts by volume of tetrahydrofuran, 7.5 parts by volume of 25% sodium hydroxide, and 7.5 parts by volume of water. The salts which form are filtered off and the filtrate is dried over anhydrous magnesium sulfate and concentrated under reduced pressure to yield clear oil. The oil is taken up in ether and treated with isopropanolic hydrogen chloride to give, as a white solid, 2-benzyl-8-phenyl-1,2,3,4-tetrahydroisoquinoline hydrochloride, melting at about 187°-189° C. after recrystallization from a mixture of ethanol and ether. This compound has the following formula Substitution of an equivalent quantity of the appropriate 3,4-dihydro-1(2H)-isoquinolone in the above detailed pressure and substantial repetition of that procedure affords the following compounds;

2-benzyl-3-methyl-8-phenyl-1,2,3,4-tetrahydroisoquinoline hydrochlorde, melting at about 194.5°-197° C. after recrystallization from a mixture of ethanol and ether;

2-benzyl-8-(o-methoxyphenyl)-1,2,3,4-tetrahydroisoquinoline hydrochloride, melting at about 213°-215° C. after recrystallization from a mixture of ethanol and ether;

2-benzyl-8-(m-methoxyphenyl)-1,2,3,4-tetrahydroisoquinoline hydrochloride melting at about 199°-202° C. after recrystallization from a mixture of ethanol and ether;

2-benzyl-8-(p-chlorophenyl)-1,2,3,4-tetrahydroisoquinoline hydrochloride;

2-benzyl-8-(m-methylphenyl)-1,2,3,4-tetrahydroisoquinoline hydrochloride;

2-benzyl-3-ethyl-8-phenyl-1,2,3,4-tetrahydroisoquinoline hydrochloride;

2-benzyl-8-(m-bromphenyl)-1,2,3,4-tetrahydroisoquinoline hydrochloride;

2-benzyl-3,6-dimethyl-8-phenyl-1,2,3,4-tetrahydroisoquinoline hydrochloride;

2-benzyl-7-methoxy-8-phenyl-1,2,3,4-tetrahydroisoquinoline hydrochloride;

2-benzyl-6,7-dimethyl-8-phenyl-1,2,3,4-tetrahydroisoquinoline hydrochloride;

2-benzyl-7-methoxy-8-(o-methoxyphenyl)-1,2,3,4-tetrahydroisoquinoline hydrochloride; and 2-benzyl-8-phenyl-3-propyl-1,2,3,4-tetrahydroisoquinoline hydrochloride.

EXAMPLE 9

A mixture of 6.20 parts of 2-benzyl-8-phenyl-1,2,3,4-tetrahydroisoquinoline hydrochloride and 0.62 parts of 5% palladium-on-carbon catalyst in 100 parts by volume of ethanol is hydrogenated at 2 psi and ambient temperature for about 6 hours. The filtered reaction solution is concentrated to 75 parts by volume and after the addition of ether crystalline solid is formed. This solid is recrystallized from ethanol to yield 8-phenyl-1,2,3,4-tetrahydroisoquinoline hydrochloride, as white crystals melting at about 268°-270° C. This compound has the following formula

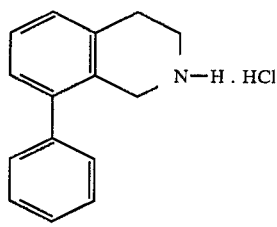

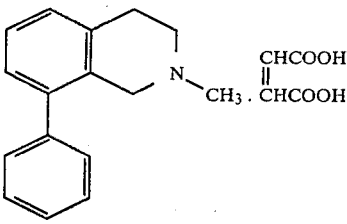

Substitution of an equivalent quantity of the appropriate tetrahydroisoquinoline hydrochloride in the above detailed procedure and substantial repetition of that procedure afford the following compounds:

3-methyl-8-phenyl-1,2,3,4-tetrahydroisoquinoline hydrochloride, melting at about 276.5°–279° C. after recrystallization from ethanol;

8-(o-methoxyphenyl)-1,2,3,4-tetrahydroisoquinoline hydrochloride, melting at about 209.5°–210.5° C.;

8-(m-methoxyphenyl)-1,2,3,4-tetrahydroisoquinoline hydrochloride, melting at about 192.5°–193.5° C.;

8-(p-chlorophenyl)-1,2,3,4-tetrahydroisoquinoline hydrochloride;

8-(m-methylphenyl)-1,2,3,4-tetrahydroisoquinoline hydrochloride;

3-ethyl-8-phenyl-1,2,3,4-tetrahydroisoquinoline hydrochloride;

8-(m-bromophenyl)-1,2,3,4-tetrahydroisoquinoline hydrochloride;

3,6-dimethyl-8-phenyl-1,2,3,4-tetrahydroisoquinoline hydrochloride;

7-methoxy-8-phenyl-1,2,3,4-tetrahydroisoquinoline hydrochloride;

6,7-dimethyl-8-phenyl-1,2,3,4-tetrahydroisoquinoline hydrochloride;

7-methoxy-8-(o-methoxyphenyl)-1,2,3,4-tetrahydroisoquinoline hydrochloride; and 8-phenyl-3-propyl-1,2,3,4-tetrahydroisoquinoline hydrochloride.

EXAMPLE 10

A mixture of 2.87 parts of 8-phenyl-1,2,3,4-tetrahydroisoquinoline hydrochloride, 1.8 part of 90% formic acid and 1.35 part of 37% aqueous formaldehyde is stirred at ambient temperature overnight. The mixture is then warmed on a steam bath for about 2 hours, cooled, and 1.5 part of concentrated hydrochloric acid is added. The excess formic acid and formaldehyde are distilled off under reduced pressure. The residue is taken up in water and the solution is made alkaline with 50% sodium hydroxide and extracted with ether. The extract is washed with water, dried over anhydrous magnesium sulfate and the solvent removed under reduced pressure to give clear colorless oil. The oil is taken up in ether and treated with a saturated solution of maleic acid in ether. The crystalline solid which forms is 2-methyl-8-phenyl-1,2,3,4-tetrahydroisoquinoline maleate. The compound melts at about 146.5°–147.5° C. after recrystallization from acetonitrile and has the following formula Substitution of an equivalent quantity of the appropriate tetrahydroisoquinoline hydrochloride in the above detailed procedure and treatment with the appropriate acid affords the following compounds:

2,3-dimethyl-8-phenyl-1,2,3,4-tetrahydroisoquinoline hydrobromide, melting at about 190°–192° C. after recrystallization from a mixture of ethanol and ether;

8-(o-methoxyphenyl)-2-methyl-1,2,3,4-tetrahydroisoquinoline hydrochloride melting at about 212°–213° C. after recrystallization from a mixture of ethanol and ether;

8(m-methoxyphenyl)-2-methyl-1,2,3,4-tetrahydroisoquinoline hydrochloride, melting at about 196.5°–197.5° C. after recrystallization from a mixture of ethanol and ether 8-(p-chlorophenyl)-2-methyl-1,2,3,4-tetrahydroisoquinoline maleate;

8-(m-methylphenyl)-2-methyl-1,2,3,4-tetrahydroisoquinoline maleate;

3-ethyl-2-methyl-8-phenyl-1,2,3,4-tetrahydroisoquinoline maleate;

8-(m-bromophenyl)-2-methyl-1,2,3,4-tetrahydroisoquinoline maleate;

2,3,6-trimethyl-8-phenyl-1,2,3,4-tetrahydroisoquinoline maleate;

7-methoxy-2-methyl-8-phenyl-1,2,3,4-tetrahydroisoquinoline maleate;

2,6,7-trimethyl-8-phenyl-1,2,3,4-tetrahydroisoquinoline maleate;

7-methoxy-8-(o-methoxyphenyl)-2-methyl-1,2,3,4-tetrahydroisoquinoline maleate; and 2-methyl-8-phenyl-3-propyl-1,2,3,4-tetrahydroisoquinoline maleate.

EXAMPLE 11

A solution of 4.2 parts of 8-phenyl-1,2,3,4-tetrahydroisoquinoline and 4 parts of triethylamine in 90 parts by volume of methylene chloride is cooled in an ice bath with stirring and 1.7 part of acetyl chloride in 10 parts by volume of methylene chloride is added slowly. The mixture is allowed to warm to ambient temperature and stirred for about 2 hours. The reaction solution is washed four times with 20 parts by volume portions of water and then dried over anhydrous magnesium sulfate. The solvent is removed under reduced pressure to afford 2-acetyl-8-phenyl-1,2,3,4-tetrahydroisoquinoline.

2.1 parts of lithium aluminum hydride is added to a solution of 4.5 parts of 2-acetyl-8-phenyl-1,2,3,4-tetrahydroisoquinoline in 100 parts by volume of dry tetrahydrofuran. The resulting micture is stirred at reflux temperature for about 5 hours, then cooled in an ice bath and treated successively with 4.2 parts by volume of water in 8.4 parts by volume of tetrahydrofuran, 4.2 parts by volume of 25% sodium hydroxide and 4.2 parts by volume of water. The solid which forms is filtered off and washed with tetrahydrofuran. The combined tetrahydrofuran portions are concentrated under reduced pressure and the resulting oil taken into ether and treated with isopropanolic hydrogen chloride. The solid which forms is collected by filtration and recrystallized from a mixture of ethanol and ether to give 2-ethyl-8-phenyl-1,2,3,4-tetrahydroisoquinoline hydrochloride as white crystals. This compound has the following structural formula

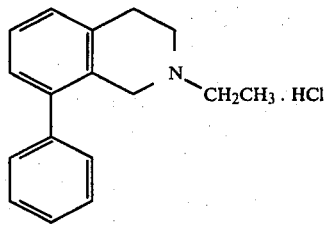

Substitution of equivalent quantities of the appropriate 8-aryl-1,2,3,4-tetrahydroisoquinoline and the appropriate alkanoyl chloride in the above detailed procedure and substantial repetition of that procedure affords the following compounds:

2-ethyl-3-methyl-8-phenyl-1,2,3,4-tetrahydroisoquinoline hydrochloride;
2-ethyl-8-(o-methoxyphenyl)-1,2,3,4-tetrahydroisoquinoline hydrochloride;
2-ethyl-8-(m-methoxyphenyl)-1,2,3,4-tetrahydroisoquinoline hydrochloride;
2-propyl-8-phenyl-1,2,3,4-tetrahydroisoquinoline hydrochloride;
2-propyl-8-(p-chlorophenyl)-1,2,3,4-tetrahydroisoquinoline hydrochloride;
2,3-diethyl-8-phenyl-1,2,3,4-tetrahydroisoquinoline hydrochloride;
2-ethyl-3,6-dimethyl-8-phenyl-1,2,3,4-tetrahydroisoquinoline hydrochloride;
2-ethyl-7-methoxy-8-phenyl-1,2,3,4-tetrahydroisoquinoline hydrochloride.

What is claimed is:

1. A compound of the formula

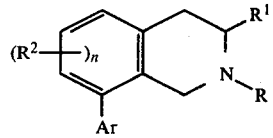

and the non-toxic pharmacologically acceptable acid addition salts thereof; wherein R is hydrogen, benzyl, or an alkyl group of 1 to 7 carbon atoms, $R^1$ is hydrogen or an alkyl group of 1 to 7 carbon atoms; $R^2$ in each occurrence is, alike or different, hydrogen, and alkyl group of 1 to 7 carbon atoms or alkoxy group of 1 to 7 carbon atoms; Ar is phenyl unsubstituted or substituted with up to 5 halogens alkyl groups of 1 to 7 carbon atoms, or alkoxy groups of 1 to 7 carbon atoms; and n is positive integer 1,2 or 3.

2. A compound according to claim 1 having the formula

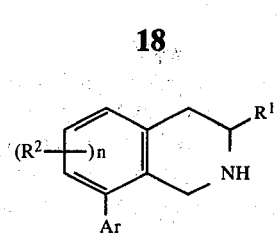

and the non-toxic pharmacologically acceptable acid addition salts thereof; wherein $R^1$ is hydrogen or an alkyl group of 1 to 7 carbon atoms; $R^2$ in each occurrence is, alike or different, hydrogen, an alkyl group of 1 to 7 carbon atoms or alkoxy group of 1 to 7 carbom atoms; Ar is phenyl unsubstituted or substituted with up to 5 halogens, alkyl groups of 1 to 7 atoms, or alkoxy groups of 1 to 7 carbon atoms; and n is positive integer 1, 2 or 3.

3. A compound according to claim 1 having the formula

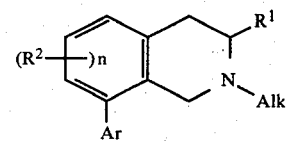

and the non-toxic pharmacologically acceptable acid addition salts thereof; wherein Alk is an alkyl group of 1 to 7 carbon atoms; $R^1$ is hydrogen or an alkyl group of 1 to 7 carbon atoms; $R^2$ in each occurrence is, alike or different, hydrogen, an alkyl group of 1 to 7 carbon atoms or alkoxy group of 1 to 7 carbon atoms; Ar is phenyl unsubstituted or substituted with one or more halogen up to 5 halogens, alkyl groups of 1 to 7 carbon atoms, or alkoxy groups of 1 to 7 carbon atoms; and n is positive integer 1,2 or 3.

4. A compound according to claim 1 having the formula

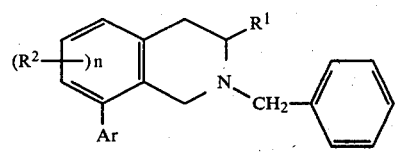

and the non-toxic pharmacologically acceptable acid addition salts thereof; wherein $R^1$ is hydrogen or an alkyl group of 1 to 7 carbon atoms; $R^2$ in each occurrence is, alike or different, hydrogen, an alkyl group of 1 to 7 carbon atoms or alkoxy group of 1 to 7 carbon atoms; Ar is phenyl unsubstituted or substituted with up to 5 halogens, alkyl groups of 1 to 7 carbon atoms or alkoxy groups of 1 to 7 carbon atoms, and n is positive integer 1, 2 or 3.

5. A compound according to claim 1 having the formula

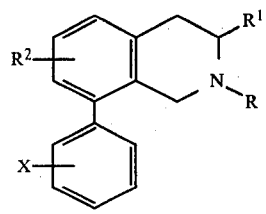

and the non-toxic pharmacologically acceptable acid addition salts thereof; wherein R is hydrogen, benzyl or an alkyl group of 1 to 7 carbon atoms; R¹ is hydrogen or an alkyl group of 1 to 7 carbon atoms; and X is hydrogen, halogen, an alkyl group of 1 to 7 carbon atoms, or alkoxy group of 1 to 7 carbon atoms; and R² is hydrogen, an alkyl group of 1 to 7 carbon atoms or alkoxy group of 1 to 7 carbon atoms.

6. A compound according to claim 1 having the formula

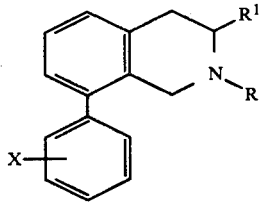

and the non-toxic pharmacologically acceptable acid addition salts thereof; wherein R is hydrogen, benzyl or an alkyl group of 1 to 7 carbon atoms; R¹ is hydrogen or an alkyl group of 1 to 7 carbon atoms; and X is hydrogen, halogen an alkyl group of 1 to 7 carbon atoms or alkoxy group of 1 to 7 carbon atoms.

7. A compound according to claim 6 which is 8-phenyl-1,2,3,4-tetrahydroisoquinoline and the non-toxic pharmacologically acceptable acid addition salts thereof.

8. A compound according to claim 6 which is 2-benzyl-8-phenyl-1,2,3,4-tetrahydroisoquinoline and the non-toxic pharmacologically acceptable acid addition salts thereof.

9. A compound according to claim 6 which is 2-methyl-8-phenyl-1,2,3,4-tetrahydroisoquinoline and the non-toxic pharmacologically acceptable acid addition salts thereof.

10. A compound according to claim 6 which is 3-methyl-8-phenyl-1,2,3,4-tetrahydroisoquinoline and the non-toxic pharmacologically acceptable acid addition salts thereof.

11. A compound according to claim 6 which is 2,3-dimethyl-8-phenyl-1,2,3,4-tetrahydroisoquinoline and the non-toxic pharmacologically acceptable acid addition salts thereof.

12. A compound according to claim 6 which is 2-benzyl-3-methyl-8-phenyl-1,2,3,4-tetrahydroisoquinoline and the non-toxic pharmacologically acceptable acid addition salts thereof.

13. A compound according to claim 6 which is 8-(o-methoxyphenyl)-1,2,3,4-tetrahydroisoquinoline and the non-toxic pharmacologically acceptable and addition salts thereof.

14. A compound according to claim 6 which is 8-(o-methoxyphenyl)-2-methyl-1,2,3,4-tetrahydroisoquinoline and the non-toxic pharmacologically acceptable acid addition salts thereof.

15. A compound according to claim 6 which is 2-benzyl-8-(o-methoxyphenyl)-1,2,3,4-tetrahydroisoquinoline and the non-toxic pharmacologically acceptable acid addition salts thereof.

16. A compound according to claim 6 which is 8-(m-methoxyphenyl)-1,2,3,4-tetrahydroisoquinoline and the non-toxic pharmacologically acceptable acid addition salts thereof.

17. A compound according to claim 6 which is 8-(m-methoxyphenyl)-2-methyl-1,2,3,4-tetrahydroisoquinoline and the non-toxic pharmacologically acceptable acid addition salts thereof.

18. A compound according to claim 6 which is 2-benzyl-8-(m-methoxyphenyl)-1,2,3,4-tetrahydroisoquinoline and the non-toxic pharmacologically acceptable acid addition salts thereof.

* * * * *